United States Patent
Chodkowski et al.

(10) Patent No.: US 11,484,677 B2
(45) Date of Patent: Nov. 1, 2022

(54) ADHESIVE PATIENT INTERFACE ASSEMBLY WITH REMOVAL TABS

(71) Applicant: KONINKLIJKE PHILIPS N.V., Eindhoven (NL)

(72) Inventors: Lauren Patricia Chodkowski, Pittsburgh, PA (US); Natasha A. Gilbert, Monroeville, PA (US)

(73) Assignee: Koninklijke Philips N.V., Eindhoven (NL)

( * ) Notice: Subject to any disclaimer, the term of this patent is extended or adjusted under 35 U.S.C. 154(b) by 220 days.

(21) Appl. No.: 16/822,521

(22) Filed: Mar. 18, 2020

(65) Prior Publication Data
US 2020/0306484 A1    Oct. 1, 2020

Related U.S. Application Data
(60) Provisional application No. 62/825,230, filed on Mar. 28, 2019.

(51) Int. Cl.
*A61M 16/06*    (2006.01)

(52) U.S. Cl.
CPC .............................. *A61M 16/0688* (2014.02)

(58) Field of Classification Search
CPC .... A61M 16/0688; A61M 16/06–0694; A61M 2016/0661; A62B 18/02; A62B 18/025; A62B 23/02; A62B 23/025
See application file for complete search history.

(56) References Cited

U.S. PATENT DOCUMENTS

| | | | |
|---|---|---|---|
| 5,743,885 A | 4/1998 | Hoerby | |
| 5,772,623 A | 6/1998 | Conte | |
| 6,196,223 B1 * | 3/2001 | Belter | A41D 13/1176 |
| | | | 128/205.25 |
| 8,061,357 B2 | 11/2011 | Doshi et al. | |
| 8,381,732 B2 | 2/2013 | Daly | |
| 8,966,662 B2 | 3/2015 | Belliappa | |
| 9,849,260 B2 * | 12/2017 | Black | A61M 16/0616 |
| 2002/0185134 A1 * | 12/2002 | Bishop | A61M 16/06 |
| | | | 128/206.25 |
| 2008/0041373 A1 | 2/2008 | Pierce et al. | |
| 2008/0302365 A1 * | 12/2008 | Cohen | A61M 16/0616 |
| | | | 128/206.12 |
| 2012/0180795 A1 | 7/2012 | Knight | |
| 2018/0229007 A1 | 8/2018 | Bizarria et al. | |
| 2018/0353721 A1 | 12/2018 | Barlow et al. | |
| 2019/0076616 A1 * | 3/2019 | Walters | A61M 16/0688 |

OTHER PUBLICATIONS

International Search Report for PCT/EP2020/058740 dated Mar. 27, 2020.

\* cited by examiner

*Primary Examiner* — Valerie L Woodward
(74) *Attorney, Agent, or Firm* — Michael W. Haas

(57) ABSTRACT

An adhesive arrangement for use in securing a patient interface to the face of a patient includes a substrate material having a first surface that is structured to face the patient and a second surface opposite the first surface. The substrate material includes a number of tabs, each tab projecting outward from a main portion of the substrate material. The adhesive arrangement further includes an adhesive material disposed on the first surface of the substrate material. Each of the tabs is sized and configured to be folded back onto a corresponding portion of the main portion of the substrate material and coupled thereto by the adhesive material.

16 Claims, 4 Drawing Sheets

ADHESIVE PATIENT INTERFACE ASSEMBLY WITH REMOVAL TABS

CROSS-REFERENCE TO RELATED APPLICATIONS

This patent application claims the priority benefit under 35 U.S.C. § 119(e) of U.S. Provisional Application No. 62/825,230, filed on Mar. 28, 2019, the contents of which are herein incorporated by reference.

BACKGROUND OF THE INVENTION

1. Field of the Invention

The present invention relates to adhesive arrangements for use in securing a patient interface device, used in delivering a flow of breathing gas to the airway of the patient, to the face of the patient and, more particularly, to adhesive arrangements having removal tabs for assisting in the removal of such adhesive arrangements from the skin of the patient.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether obstructive, central, or mixed, which is a combination of obstructive and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring.

It is well known to treat sleep disordered breathing by applying a continuous positive air pressure (CPAP) to the patient's airway. This positive pressure effectively "splints" the airway, thereby maintaining an open passage to the lungs. It is also known to provide a positive pressure therapy in which the pressure of gas delivered to the patient varies with the patient's breathing cycle, or varies with the patient's breathing effort, to increase the comfort to the patient. This pressure support technique is referred to as bi-level pressure support, in which the inspiratory positive airway pressure (IPAP) delivered to the patient is higher than the expiratory positive airway pressure (EPAP). It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing.

Pressure support therapies as just described typically involve the placement of a patient interface device including a mask component having a soft, flexible sealing cushion member on the face of the patient. The mask component may be, without limitation, a nasal mask that covers the patient's nose, a nasal/oral mask that covers the patient's nose and mouth, or a full face mask that covers the patient's face. Such patient interface devices may also employ other patient contacting components, such as forehead supports, cheek pads and chin pads. The patient interface device is connected to a gas delivery tube or conduit and interfaces the pressure support device with the airway of the patient, so that a flow of breathing gas can be delivered from the pressure/flow generating device to the airway of the patient.

Traditionally, such patient interface devices have been secured to the face/head of the patient by a headgear component having one or more straps which wrap around all, or a portion, of the patient's head. Recently, adhesive arrangements have been employed, either in-whole, or in-part, to secure patient interface devices to the face of a patient. In such arrangements the largest concerns/complaints are related to the strength of the adhesive and the ease of removal of the adhesive. Such concerns create a balancing act as the adhesive must be strong enough to stay adhered to the patient, and thus keep the patient interface device secured to the patient, but also must be easy to remove at the end of use. A large deterrent of adhesive CPAP masks is how difficult it is to remove the adhesive and the resulting skin irritation after a difficult removal.

SUMMARY OF THE INVENTION

Accordingly, as one aspect of the present invention an adhesive arrangement for use in securing a patient interface to the face of a patient is provided. The adhesive arrangement comprises: a substrate material having a first surface structured to face the patient and a second surface opposite the first surface, the substrate material having a number of tabs, each tab projecting outward from a main portion of the substrate material; and an adhesive material disposed on the first surface of the substrate material. Each of the tabs is sized and configured to be folded back onto a corresponding portion of the main portion of the substrate material and coupled thereto by the adhesive material.

When folded back onto the corresponding portion of the main portion of the substrate material, each tab may be surrounded by about 180 degrees by the adhesive material. When folded back onto the corresponding portion of the main portion of the substrate material, each tab may be surrounded by at least 180 degrees by the adhesive material. Each of the tabs may be semi-circular in shape.

The number of tabs may each be delineated from the main portion by a number of delineations provided on or in the substrate material. The number of delineations may comprise one or more of: indicia, grooving, scoring, or perforations.

As another aspect of the present invention, a patient interface assembly is provided. The patient interface assembly comprises: a patient interface for communicating a flow of a breathing gas to the airway of a patient; and an adhesive arrangement coupled to the patient interface for securing the patient interface to the face of the patient. The adhesive arrangement comprises: a substrate material having a first surface structured to face the patient and a second surface opposite the first surface, the substrate material having a number of tabs, each tab projecting outward from a main portion of the substrate material; and an adhesive material disposed on the first surface of the substrate material. Each of the tabs are sized and configured to be folded back onto a corresponding portion of the main portion of the substrate material and coupled thereto by the adhesive material.

The adhesive arrangement may be coupled to the patient interface via a second adhesive material disposed on the second surface of the substrate material.

Each of the tabs may be semi-circular in shape. When folded back onto the corresponding portion of the main portion of the substrate material, each tab may be surrounded by about 180 degrees by the adhesive material. When folded back onto the corresponding portion of the main portion of the substrate material, each tab is surrounded by at least 180 degrees by the adhesive material.

Each tab of the number of tabs may be delineated from the main portion by a number of delineations provided on or in the substrate material. The number of delineations may comprise one or more of: indicia, grooving, scoring, or perforations.

As yet another aspect of the present invention, an airway pressure support system is provided. The airway pressure support system comprises: a gas flow generator structured to generate a flow of breathing gas; a hose having a first end coupled to the gas flow generator and an opposite second end; and a patient interface assembly coupled to the second end of the hose which is structured to receive the flow of breathing gas communicated by the hose from the gas flow generator. The patient interface assembly comprises: a patient interface for communicating a flow of a breathing gas to the airway of a patient; and an adhesive arrangement coupled to the patient interface for securing the patient interface to the face of the patient. The adhesive arrangement comprises: a substrate material having a first surface structured to face the patient and a second surface opposite the first surface, the substrate material having a number of tabs, each tab projecting outward from a main portion of the substrate material; and an adhesive material disposed on the first surface of the substrate material. Each of the tabs is sized and configured to be folded back onto a corresponding portion of the main portion of the substrate material and coupled thereto by the adhesive material.

The adhesive arrangement may be coupled to the patient interface via a second adhesive material disposed on the second surface of the substrate material.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF EXEMPLARY EMBODIMENTS

Figure 1:
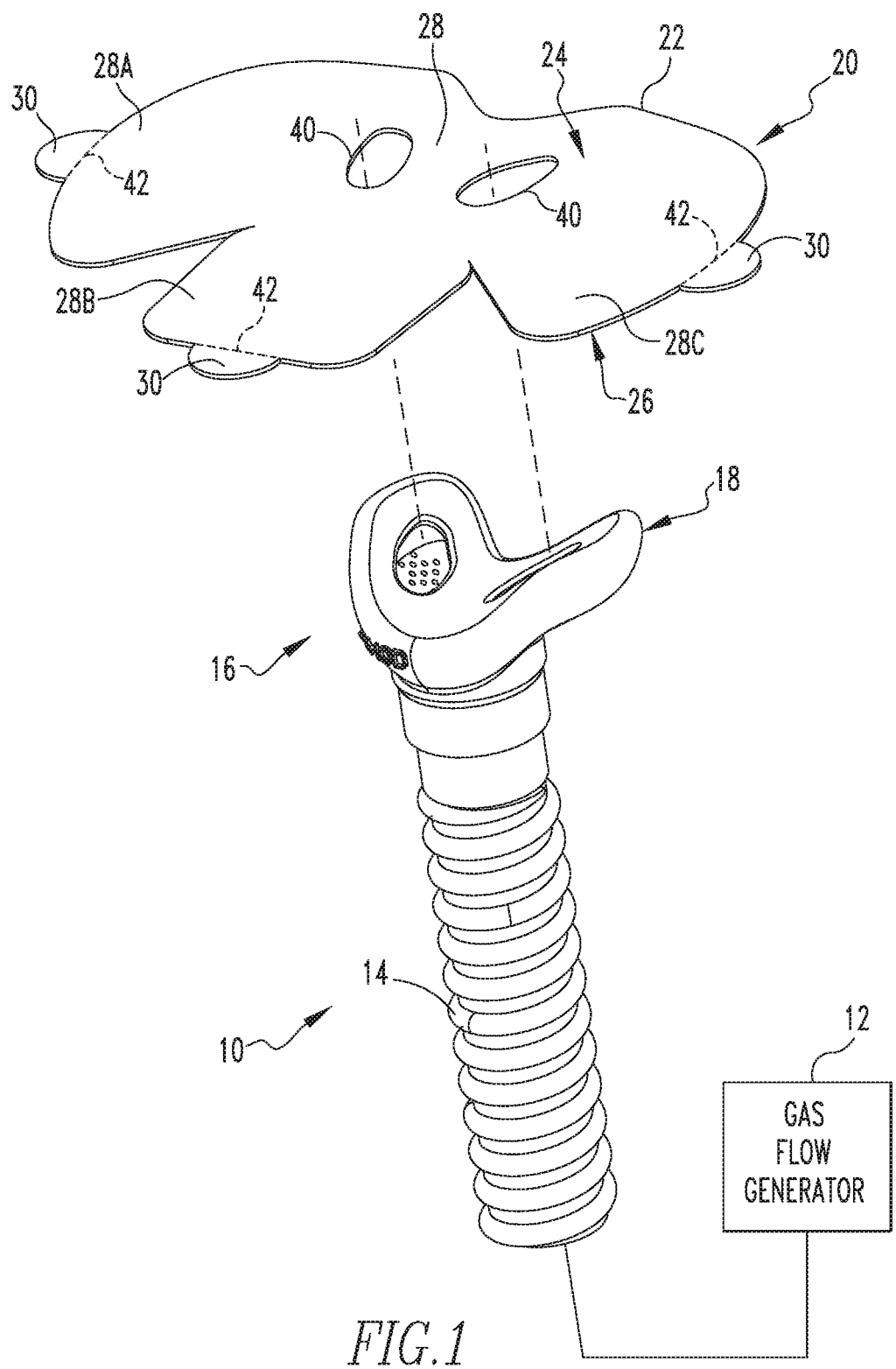
FIG. 1 is a simplified perspective front view of an airway pressure support system including a patient interface having an adhesive arrangement including removal tabs, in accordance with one non-limiting example embodiment of the present invention, shown exploded therefrom.

As required, detailed embodiments of the present invention are disclosed herein; however, it is to be understood that the disclosed example embodiments described herein are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are coupled directly in contact with each other. As used herein, "fixedly coupled" or "fixed" means that two components are coupled so as to move as one while maintaining a constant orientation relative to each other.

As used herein, the statement that two or more parts or components "engage" one another shall mean that the parts exert a force against one another either directly or through one or more intermediate parts or components. As used herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a simplified perspective front view of an airway pressure support system 10 in accordance with one non-limiting embodiment of the disclosed concept for use in providing a flow of a breathing gas to the airway of a patient (not shown). Airway pressure support system 10 includes a gas flow generator 12 (shown in simplified form) and a hose 14 (also shown in simplified form) having a first end (not numbered) coupled to gas flow generator 12 and an opposite second end (not numbered). Gas flow generator 12 is structured to generate a flow of breathing gas to be delivered to an airway of a patient via hose 14 and a patient interface assembly 16 coupled to the second end of hose 14. Accordingly, airway pressure support system 10 further includes patient interface assembly 16 for communicating the flow of breathing gas from hose 14 and gas flow generator 12 to the airway of a patient.

Patient interface assembly 16 includes a patient interface 18 which, in the example embodiment shown in FIG. 1, is in the form of a cradle-like interface for generally engaging the underside of the nose of a patient and providing treatment gas individually to each of the nares of a patient. It is to be appreciated however, that patient interface 18 is provided for exemplary purposes only and that other patient interfaces (e.g., without limitation, nasal masks, oral/nasal masks, nasal pillows mask, etc.) may be employed without varying from the scope of the present invention. Patient interface assembly 16 further includes an adhesive arrangement 20 coupled to patient interface 18 for securing patient interface 18 to the face of a patient. In the example embodiment illustrated in FIG. 1, adhesive arrangement 20 is structured to be positioned generally between patient interface 16 and the skin of the patient and is coupled to patient interface 16 via an adhesive (discussed further below), however, it is to be appreciated that adhesive arrangement 20 may be otherwise positioned depending on the arrangement of the patient interface employed as patient interface 18 without varying from the scope of the present invention. Hence, it is also to be appreciated that the coupling between adhesive arrangement 20 and patient interface 18 may be accomplished via any other suitable coupling arrangement which preferably provides for adhesive arrangement 20 to be uncoupled from patient interface 18 and discarded, thus allowing for coupling of a new/unused adhesive arrangement 20 to patient interface 18 as needed (e.g., without limitation for every treatment session).

Figure 2A:
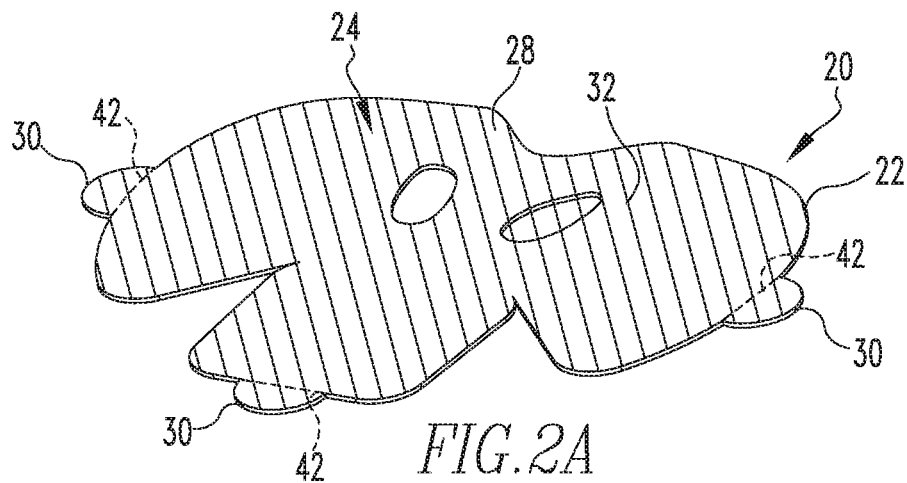
FIG. 2A is a partially schematic, simplified perspective view of the patient facing side of the adhesive arrangement of FIG. 1 shown with portions thereof disposed in an initial, first positioning.
Figure 3A:
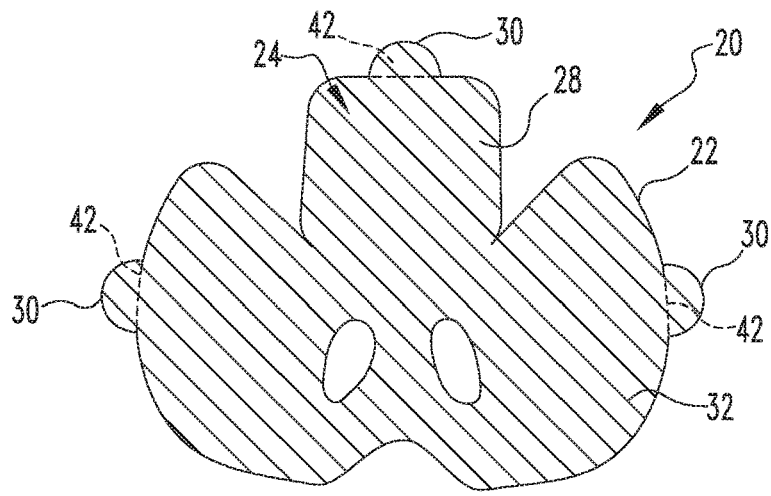
FIG. 3A is a partially schematic, simplified plan view of the patient facing side of the adhesive arrangement of FIG. 2A.

Continuing to refer to FIG. 1, as well as to FIGS. 2A and 3A, adhesive arrangement 20 is formed from a generally thin (e.g., having a thickness of at least 0.04 mm) substantially planar substrate material 22 having a first planar surface 24, which faces toward a patient, and a second planar surface 26, opposite first planar surface 24. Planar substrate material 22 may generally be any plyable material such as, for example, without limitation, foam, silicone polyurethane, latex, or any other suitable material. Planar substrate material 22 includes a main portion 28 having a number of tabs 30 projecting outward therefrom.

Figure 2B:
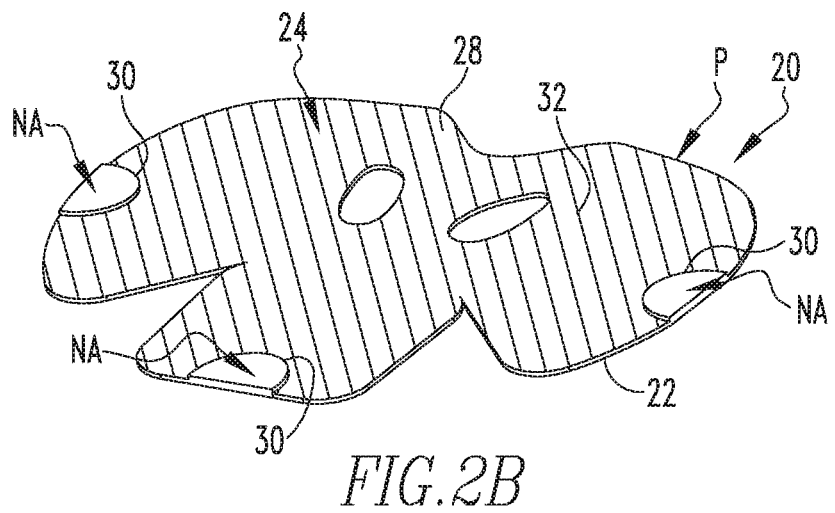
FIG. 2B is a partially schematic, simplified perspective view of the patient facing side of the adhesive arrangement of FIG. 2A shown with the portions thereof disposed in a second positioning.
Figure 2C:
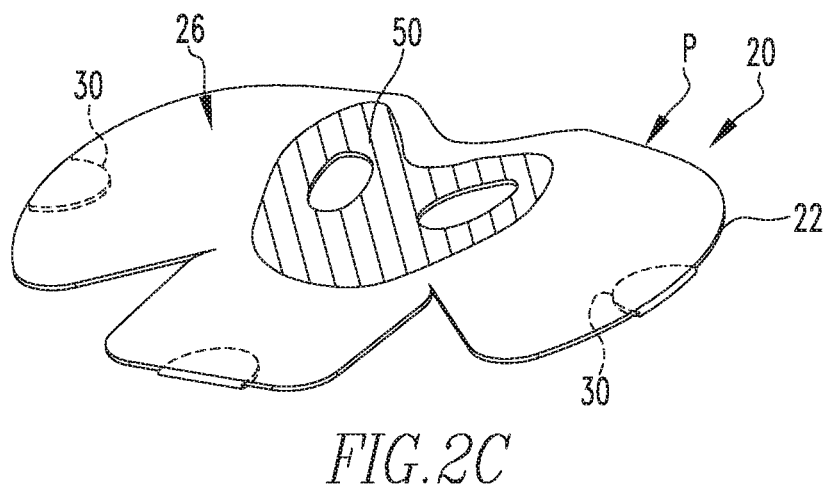
FIG. 2C is a partially schematic, simplified perspective view of the side facing away from the patient of the adhesive arrangement of FIG. 2A shown with the portions thereof disposed in the second positioning of FIG. 2B.
Figure 3B:
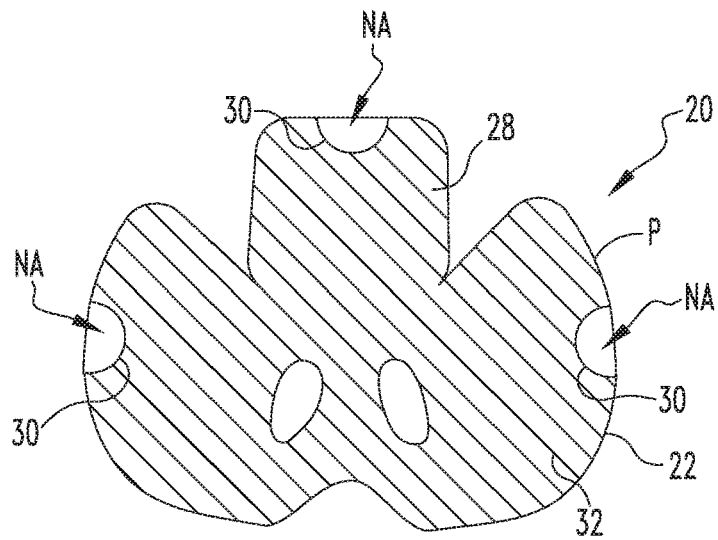
FIG. 3B is a partially schematic, simplified plan view of the patient facing side of the adhesive arrangement of FIG. 2B.
Figure 3C:
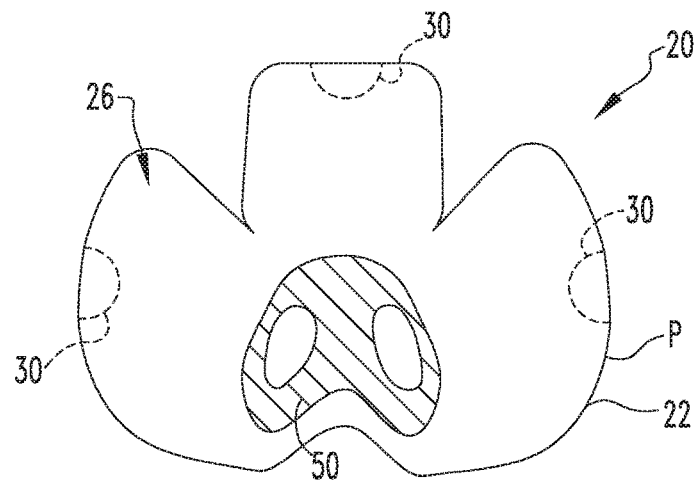
FIG. 3C is a partially schematic, simplified plan view of the side facing away from the patient of the adhesive arrangement of FIG. 3B.

Adhesive arrangement 20 further includes an adhesive material 32 (shown schematically as hatching in FIGS. 2A, 2B, 3A, and 3B, e.g., without limitation, a silicone or acrylic based adhesive layer or any other suitable adhesive layer) provided on first planar surface 24 for adhering adhesive arrangement 20 to the skin of a patient. Prior to adhering substrate material 22 to the skin of a patient, each tab 30 is folded back onto main portion 28 such that the adhesive material 32 on tab 30 is adhered to the adhesive material 32 on main portion 28, thus fixing each tab 30 in a positioning on first planar surface 24 such as shown in FIGS. 2B and 3B. As adhesive material 32 is only disposed on first planar surface 24 portion of each tab and not on the second planar surface 26 portion, such positioning of tabs 30 on first planar surface 24 as shown in FIGS. 2B and 3B effectively provides for a non-adhesive area NA extending from a periphery P of main portion 28 that is generally surrounded by adhesive material 32 by about 180 degrees, if not more. Such non-adhesive areas NA provide for an underlying area that can be readily engaged by a fingertip of a patient, and gripped via a thumb positioned on second planar surface 26 of main portion 28 opposite such non-adhesive area NA in order to peel away all, or selected portions of adhesive arrangement 20 from the skin of the patient.

Although shown generally as being semi-circular in shape in the illustrated examples, it is to be appreciated that tabs 30 may be of different shape (e.g., without limitation, semi-elliptical, rectangular, square, etc.) without varying from the scope of the present invention. Furthermore, although shown and described herein as being planar or generally planar, it is to be appreciated that substrate material 22, as well as first and second surfaces 22 and 24 thereof, may be of other shape (e.g., without limitation, curved, cupped, etc.) without varying from the scope of the present invention.

In the example shown in FIGS. 1, 2A-2C, and 3A-3C, main portion 28 is generally shaped into three petals 28A, 28B, 28C (e.g., like a flower) and includes a pair of oblong apertures 40 defined therein which are sized and positioned to generally align with the nares of a patient and provide for the passage of the flow of breathing gas from patient interface 18 to the airway of the patient. In such arrangement, each of petals 28A, 28B and 28C are sized and positioned to generally wrap up along, and be adhered around, the nose of a patient. More particularly, petal 28A is positioned to wrap up around the right side of a patient's nose, petal 28B the front of a patient's nose, and 28C the left side of a patient's nose. In such example embodiment, each of petals 28A, 28B, 28C is provided with a tab 30 and resulting non-adhesive area NA for use in removing each petal 28A, 28B, 28C, and thus adhesive arrangement 20 and patient interface 18, which is coupled to adhesive arrangement 20, from the face of a patient.

Furthermore, in the example shown in FIGS. 1, 2A-2C, and 3A-3C, a small area of an adhesive 50 (shown schematically as hatching in FIGS. 2C and 3C) is utilized to secure second planar surface 26 of adhesive arrangement 20 to patient interface 20. Additionally, in order to help distinguish and/or to assist in folding of each tab 30, each tab 30 may generally be delineated from main portion 28 of substrate material 22 by one or more delineations 42 in the form of one or more of: indicia provided on first planar surface 24; grooving, scoring, and/or perforations formed in substrate material 22; or any other suitable arrangement or arrangements.

Figure 4:
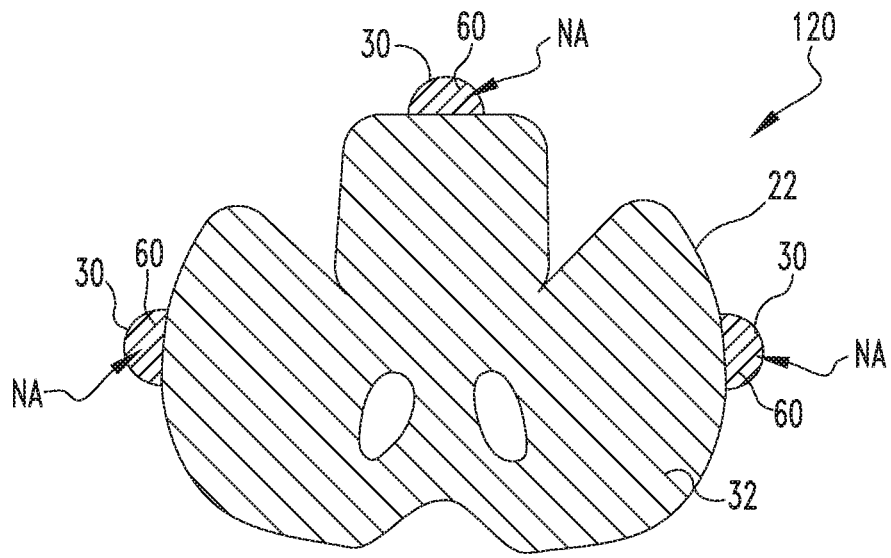
FIG. 4 is a partially schematic, simplified plan view of the patient facing side of another adhesive arrangement in accordance with one non-limiting example embodiment of the present invention.
Figure 5:
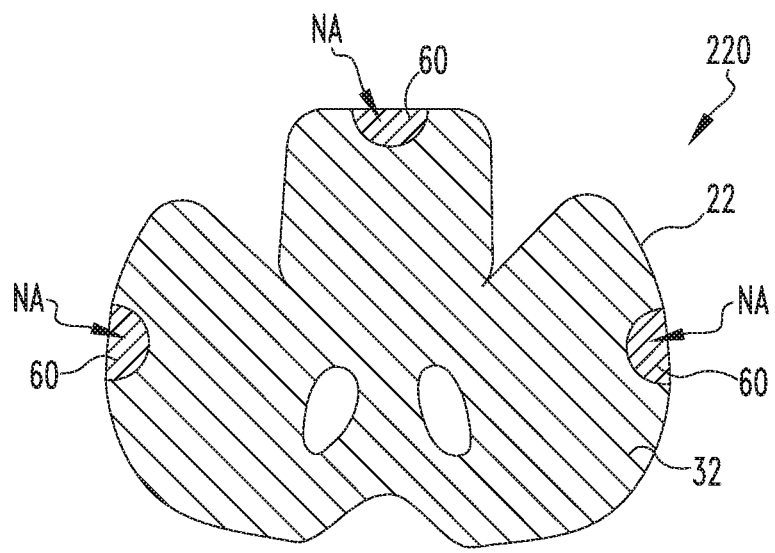
FIG. 5 is a partially schematic, simplified plan view of the patient facing side of another adhesive arrangement in accordance with one non-limiting example embodiment of the present invention.

FIGS. 4 and 5 show examples of adhesive arrangements 120 and 220 in accordance with other non-limiting examples of the present invention which utilize a layer of a release film 60 (shown schematically as hatching in FIGS. 4 and 5) disposed covering portion of adhesive material 32, in order to form non-adhesive areas NA which may be readily gripped by a patient in a manner such as previously discussed in order to remove either of adhesive arrangements 120 or 220 from the skin of a patient.

From the foregoing examples it is thus to be appreciated that the disclosed concept provides for improved adhesive arrangements for securing patient interfaces to a patient as well as patient interfaces including such adhesive arrangements.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. An adhesive arrangement for use in securing a patient interface to the face of a patient, the adhesive arrangement comprising:
    a substrate material having a first surface structured to face the patient and a second surface opposite the first surface, the substrate material having a number of tabs, each tab projecting outward from a main portion of the substrate material; and
    an adhesive material disposed on the first surface of the substrate material,
    wherein each of the tabs is sized and configured to be folded back onto a corresponding portion of the main portion of the substrate material and coupled thereto by the adhesive material,
    wherein th number of tabs are each delineated from the main portion by a number of delineations provided on or in the substrate material, and
    wherein the number of delineations comprise one or more of, grooving, scoring, or perforations defined in the substrate material.

2. The adhesive arrangement of claim 1, wherein, when folded back onto the corresponding portion of the main portion of the substrate material, each tab is surrounded by about 180 degrees by the adhesive material.

3. The adhesive arrangement of claim 1, wherein, when folded back onto the corresponding portion of the main portion of the substrate material, each tab is surrounded by at least 180 degrees by the adhesive material.

4. The adhesive arrangement of claim 1, wherein each of the tabs are semi-circular in shape.

5. An airway pressure support system comprising:
    a gas flow generator structured to generate a flow of breathing gas;
    a hose having a first end coupled to the gas flow generator and an opposite second end; and
    a patient interface assembly coupled to the second end of the hose which is structured to receive the flow of breathing gas communicated by the hose from the gas flow generator, wherein the patient interface assembly comprises:
        a patient interface for communicating a flow of a breathing gas to the airway of a patient; and
        an adhesive arrangement such as recited in claim 1 coupled to the patient interface for securing the patient interface to the face of the patient.

6. The airway pressure support system of claim 5, wherein the adhesive arrangement is coupled to the patient interface via a second adhesive material disposed on the second surface of the substrate material.

7. A patient interface assembly comprising:
    a patient interface for communicating a flow of a breathing gas to the airway of a patient; and
    an adhesive arrangement coupled to the patient interface for securing the patient interface to the face of the patient, the adhesive arrangement comprising:
        a substrate material having a first surface structured to face the patient and a second surface opposite the first surface, the substrate material having a number of tabs (30), each tab projecting outward from a main portion of the substrate material; and
        an adhesive material disposed on the first surface of the substrate material,
    wherein each of the tabs is sized and configured to be folded back onto a corresponding portion of the main portion of the substrate material and coupled thereto by the adhesive material,
    wherein the number of tabs are each delineated from the main portion by a number of delineations provided on or in the substrate material, and
    wherein the number of delineations comprise one or more of: grooving, scoring, or perforations defined in the substrate material.

8. The patient interface assembly of claim 7, wherein the adhesive arrangement is coupled to the patient interface via a second adhesive material disposed on the second surface of the substrate material.

9. The patient interface assembly of claim 7, wherein each of the tabs are semi-circular in shape.

10. The patient interface assembly of claim 7, wherein, when folded back onto the corresponding portion of the main portion of the substrate material, each tab is surrounded by about 180 degrees by the adhesive material.

11. The patient interface assembly of claim 7, wherein, when folded back onto the corresponding portion of the main portion of the substrate material, each tab is surrounded by at least 180 degrees by the adhesive material.

12. An adhesive arrangement for use in securing a patient interface to the face of a patient, the adhesive arrangement comprising:
- a substrate material having a first surface structured to face the patient and a second surface opposite the first surface, the substrate material having a main portion shaped into a plurality of petals, each petal having a number of tabs, each tab projecting outward from the main portion of the substrate material; and
- an adhesive material disposed on the first surface of the substrate material, wherein each of the tabs is sized and configured to be folded back onto a corresponding portion of the main portion of the substrate material and coupled thereto by the adhesive material.

13. The adhesive arrangement of claim 12, wherein, when folded back onto the corresponding portion of the main portion of the substrate material, each tab is surrounded by about 180 degrees by the adhesive material.

14. The adhesive arrangement of claim 12, wherein, when folded back onto the corresponding portion of the main portion of the substrate material, each tab is surrounded by at least 180 degrees by the adhesive material.

15. The adhesive arrangement of claim 12, wherein the number of tabs are each delineated from the main portion by a number of delineations provided on or in the substrate material.

16. The adhesive arrangement of claim 15, wherein the number of delineations comprise one or more of: grooving, scoring, or perforations defined in the substrate material.

* * * * *